(12) United States Patent
Potter et al.

(10) Patent No.: US 6,970,791 B1
(45) Date of Patent: Nov. 29, 2005

(54) TAILORED USER INTERFACES FOR MOLECULAR MODELING

(75) Inventors: Michael Jason Potter, North Potomac, MD (US); Hillary Sue Rodman Gilson, North Potomac, MD (US); Michael Kenneth Gilson, Gaithersburg, MD (US)

(73) Assignee: Verachem, LLC, Germantown, MD (US)

( * ) Notice: Subject to any disclaimer, the term of this patent is extended or adjusted under 35 U.S.C. 154(b) by 18 days.

(21) Appl. No.: 10/443,903

(22) Filed: May 23, 2003

(51) Int. Cl.[7] ............................................. G01N 31/00
(52) U.S. Cl. ......................................... 702/31; 707/100
(58) Field of Search .................... 702/31, 19; 707/100; 514/8; 370/395

(56) References Cited

U.S. PATENT DOCUMENTS 5,980,096 A * 11/1999 Thalhammer-Reyero .... 707/100

2001/0034580 A1 * 10/2001 Skolnick et al. .............. 702/19
2002/0048271 A1 *  4/2002 Rastinejad et al. ......... 370/395
2004/0092433 A1 *  5/2004 Wang et al. .................. 514/8

* cited by examiner

Primary Examiner—Michael Nghiem
Assistant Examiner—Xiuqin Sun
(74) Attorney, Agent, or Firm—Robin L. Teskin; Duane Morris, LLP (57) ABSTRACT

The present invention provides a method of carrying out a molecular modeling calculation and displaying the results thereof through a task-oriented user interface. The overall computational task is divided into subtasks, each of which is outfitted with a tailored graphical user interface. In a preferred implementation, the subtask user interfaces are accessed via tab icons whose layout reflects the normal order of carrying out the subtasks, and downstream subtask user-interfaces are not activated until the information they require is available from upstream subtasks. The invention also provides software that allows the user to view the setup and results of a calculation, but does not provide computational capabilities. The invention is applicable to a wide range of computational tasks.

24 Claims, 5 Drawing Sheets

Decomposition of a Molecular Modeling Task into Subtasks with Tailored Subtask Graphical User Interfaces

TAILORED USER INTERFACES FOR MOLECULAR MODELING

STATEMENT REGARDING FEDERALLY SPONSORED RESEARCH OR DEVELOPMENT

This invention was made with government support under grant GM062050, "Inexpensive, Interactive Molecular Modeling Software" awarded by the NIH. The United States government has certain rights in the invention.

CROSS-REFERENCE TO RELATED APPLICATIONS

Not Applicable

BACKGROUND OF THE INVENTION

This invention relates to methods and tools useful in the areas of computational chemistry and molecular modeling and their application to the calculation of molecular properties. More particularly, this invention relates to methods of displaying the information and controls for molecular modeling tasks in a graphical user interface.

Algorithms have been developed for computing a variety of molecular properties, and new algorithms continue to be developed. Software applications that use such algorithms are marketed commercially, largely to the pharmaceutical and chemical industries, but also to the biotechnology industry and to university laboratories. The information generated with these software applications is used to guide the development of new medications, catalysts, bioactive proteins, etc. Properties that are calculated include the 3-dimensional conformation(s) of molecules, the binding affinity of two molecules for each other, and the 3-dimensional distribution of electron density in a molecule.

Many software packages for molecular modeling are outfitted with graphical user interfaces (GUIs). Existing GUIs are similar to those of common office productivity software, such as word-processing programs, in that they provide a large central window showing whatever is being worked on, surrounded by pull-down menus and tool icons. In the case of molecular modeling software, the central window displays a graphical rendering of the molecule(s) under study, and the surrounding menus and tool icons are the controls that enable the user to set up, execute, and analyse various types of calculations. This type of GUI (hereinafter referred to as "conventional GUI") can be difficult to use because, although it enables many different molecular modeling tasks, it is not designed to make any particular task easy.

For example, a user engaged in a drug-design project may wish to predict the 3-dimensional conformations of small molecules (molecular weight<1000 Daltons) when they are bound to a protein. This computational task typically involves the following subtasks: 1) load a computer representation of the small molecules into memory from the hard drive or another source, such as a chemical draw program or an on-line database; 2) load a computer representation of the protein from the hard drive into memory; 3) designate the region of the protein into which the small molecules are expected to bind; 4) initiate and monitor the calculation; 5) view and analyze the results graphically; and 6) save the results to the hard drive. The conventional GUI requires the user to be familiar with the correct sequence of steps required to complete the task. This requirement is problematic for users who are not expert in the field. In addition, because the conventional GUI supports many different tasks, it displays a large array of graphical controls, most of which are irrelevant to any given task or subtask. There are often as many as 20–30 pull-down menus, submenus, and toolbar icons. As a consequence, finding the right control for a necessary step can involve pulling down and inspecting many different menus and sub-menus. Some trial and error is often required as well, because the brief names of menu items may not be sufficiently descriptive. Also, although the conventional GUI enables the results to be viewed, it provides no mechanism for backtracking to review how the calculation was set up and run, and to revise the setup and rerun the calculation with the selected changes. Such a capability would help the user to understand the results of a calculation in the context of the setup, and would facilitate generating a series of related calculations. Also, although the optimal graphical rendering of the molecules under study may be different at different steps in the modeling task, the rendering method is not changed automatically in the conventional molecular modeling GUI but must be changed manually by the user. In summary, although the conventional GUI is better than no GUI at all, it still poses high barriers to use, especially for people who are not expert in the field. Even for the expert, it can take a long time to learn how to use such an interface, and using it can be confusing, error-inducing, and inefficient.

Another important limitation of existing molecular simulation software is that it does not lend itself to sharing results with other users. For example, User 1 might need to share the results of a conformational study with User 2, an off-site collaborator who does not have the same modeling software. Existing molecular modeling software provides at best poor support for this usage case.

Thus, there is a need for tools that allow for guiding the user through the sequence of steps required to complete a specific molecular modeling task successfully. It would also be desirable to increase efficiency and avoid errors by helping the user to find the controls required at each step of the task. Tools allowing the user to return to previously completed steps to review and revise what has already been done would also be valuable, as would tools that allow the details and results of modeling calculations to be shared with other users who do not have access to the full-fledged software application. Tools that meet these needs would be useful for molecular modeling experts, and could also for the first time make it possible for non-experts to carry out useful molecular modeling calculations.

BRIEF SUMMARY OF THE INVENTION

The present invention provides a method of carrying out a molecular modeling calculation and displaying the results thereof through a task-oriented user interface, wherein the method comprises subdividing the calculation into subtask steps to be carried out according to a predetermined sequence by the use of calculation and display tools associated with each separate subtask, displaying the tools and results of each subtask through an individualized subtask user interface, and transferring the information generated within a selected subtask to a subtask positioned in the sequence downstream from the selected subtask. By this method, the tools and results associated with each subtask are individually viewed and used while the tools and results associated with other subtasks remain accessible but not displayed.

In another aspect of the invention, only preselected controls and/or graphics are displayed in a subtask user interface.

In another aspect of the invention, two or more subtask user interfaces are combined in a multiple-subtask user interface.

In yet another aspect of the invention, controls for selecting a subtask user interface are provided in a multiple-subtask user interface.

The invention also provides for arranging the subtask selection controls in a multiple-subtask user interface according to the predetermined sequence of subtasks.

The invention further provides for enabling the controls and/or graphics of a subtask user interface only after the calculation steps associated with an upstream subtask are completed.

In another aspect of the invention, the subtask selection controls in a multiple-subtask user interface are displayed differently, depending upon whether or not the associated subtasks are enabled.

In yet another aspect of the invention, the selections and/or intermediate results from the subtasks are viewable.

The invention also provides for disabling a subtask user interface to maintain a correct correspondence between the viewable calculation setup and the calculation results.

The invention provides in addition for clearing the settings and results downstream from a selected subtask and resuming setup and calculations from the selected subtask.

The invention also provides for storing settings and results.

In another aspect of the invention, a subtask user interface or a control in a subtask user interface is hidden and the associated subtask is executed automatically.

In yet another aspect, the invention provides for generating a printable report of the results.

In still another aspect of the present invention, a user interface different from the subtask user interfaces is provided that enables the calculation setup to be viewed along with the final results, but does not enable changes to the calculation setup or execution of the calculation.

In another aspect, the molecular modeling calculation predicts the three-dimensional conformations of a user-selected compound bound to a user-selected macromolecule of known three dimensional structure. In such calculations, the present invention also provides for interactively defining the part of the macromolecule with which the user-selected compounds interact by interactively positioning, resizing and/or reshaping a 3D object that delimits the part of the macromolecule to be studied, while viewing both the macromolecule and the 3D object in real time.

In another aspect of the invention, the molecular modeling calculation identifies from a user-supplied list those compounds that have the highest binding affinity for a user-selected macromolecule of known three-dimensional structure.

In another aspect of the invention, the molecular modeling calculation generates the chemical composition and structure of a compound likely to bind a user-selected macromolecule of known three dimensional structure.

In another aspect of the invention, the molecular modeling calculation determines the thermodynamically stable conformations of a user-supplied set of molecules.

In another aspect of the invention, the molecular modeling calculation determines the three-dimensional structures of a user-defined protein based upon the known three-dimensional structure of chemically similar protein.

The invention also provides for allowing the user to select atoms from a graphically displayed molecular system by interactively positioning a three dimensional closed object while viewing both the object and the molecular system, wherein those atoms enclosed by the form, or those molecular components partly enclosed by the form, are considered to be selected.

DETAILED DESCRIPTION OF THE INVENTION

The present invention provides a method for carrying out a molecular modeling calculation and displaying the results thereof through a task-oriented user interface. The method comprises subdividing the calculation into subtasks to be carried out in a predetermined sequence; displaying the controls and results associated with each subtask through an individual subtask user interface; and transferring the information from each subtask to all subtasks positioned downstream in the predetermined sequence. By this method, the calculation is divided into a sequence of subtasks so that the tools and results associated with each subtask can be individually viewed while the results and tools associated with other subtasks remain accessible but not displayed. One aspect of the invention allows the user to return to completed upstream subtasks in order to view and revise what has already been done. Another aspect of the invention allows the user to display the setup and results of a calculation but does not support the calculation itself; software implementing this method represents an inexpensive "viewer" which allows users who do not have a fully functional version of the software to view setup and results generated by others. Another aspect allows the user to display simplified setup options and results in order to create software applications tailored for non-expert users.

In a preferred embodiment, the user interface of the invention is configured as a series of tab icons that are always visible in the overall task-oriented user interface; each tab icon is associated with a specific subtask and the tabs are positioned from left to right in the predetermined order. Selecting a tab activates the associated subtask user interface. Subtask interfaces are disabled until the prerequisite steps are complete.

The invention also provides methods that are specifically applied to the computational tasks of predicting the three-dimensional conformations of user-selected compounds when bound to a macromolecule of known three dimensional structure; determining from a user-supplied list those compounds with higher binding affinity for a user-selected macromolecule of known three-dimensional structure; determining the thermodynamically stable conformations of a user-supplied set of molecules; determining the three-dimensional structures of user-defined proteins based upon the known three-dimensional structures of proteins with similar amino acid sequences; and generating chemical structures of new compounds likely to bind a user-selected macromolecule of known 3D structure.

Figure 1:
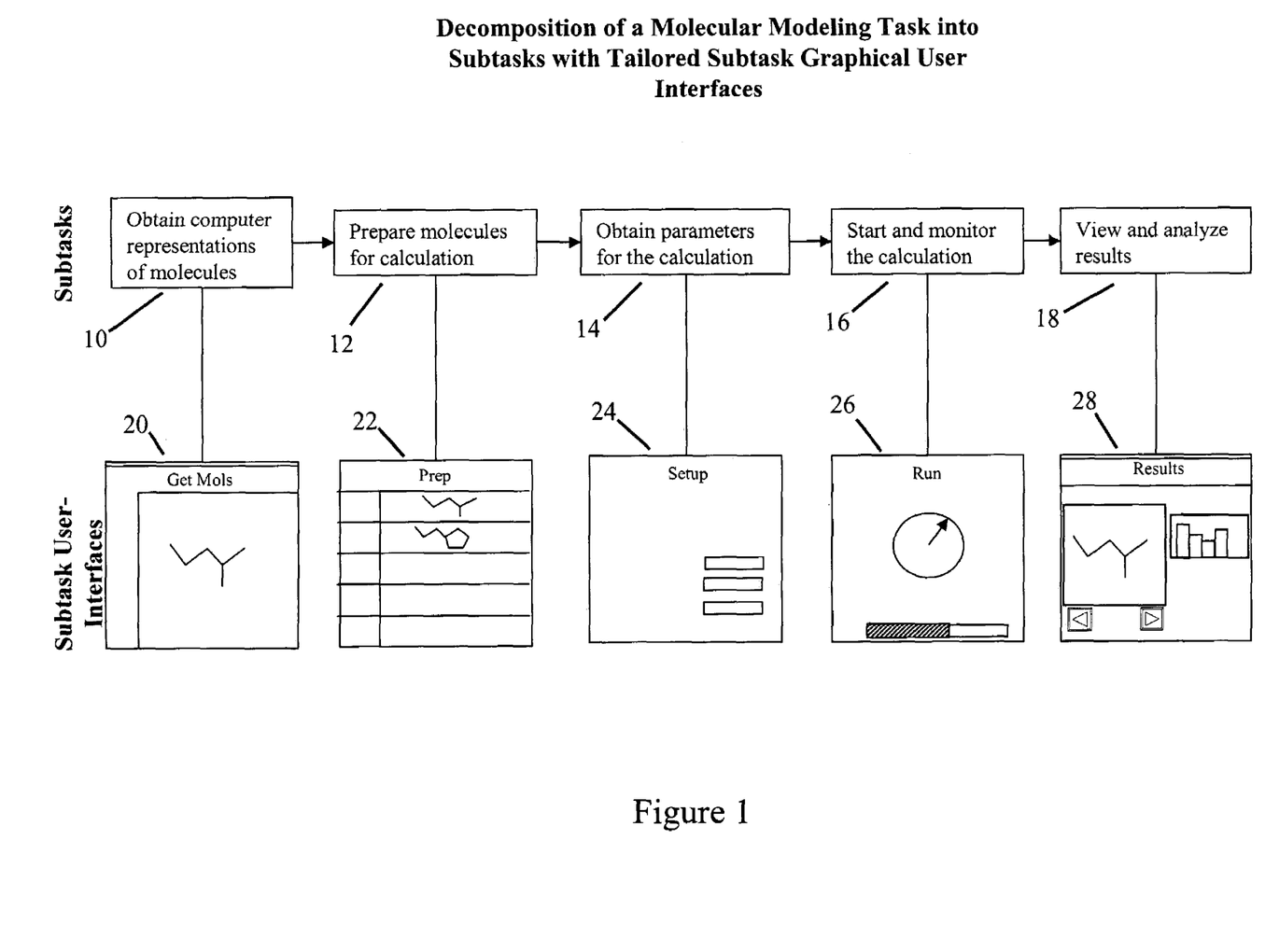
FIG. 1: Diagram of the decomposition of a typical molecular modeling task into subtasks according to the invention, with illustrative diagrams of tailored subtask user interfaces.

In one aspect of the present method, the overall computational task is divided into subtasks. FIG. 1 illustrates this division with the example of a generic molecular modeling task which is separated into the following examples of typical subtasks (10–18):

1. Load computer representations of the molecules of interest into the software application (10). The computer representation of a molecule could take the form, for example, of a list of its atoms, the bonding connections among them, and the bond orders (e.g., single or double). These representations may, for example, reside on a computer's hard drive, be retrieved from a world-wide web resource, or be provided by the user through the use of a chemical draw program.
2. Prepare the molecules for calculations (12). Examples of such preparation include the assignment of atomic parameters that allow the energy of the molecule to be calculated as a function of its conformation, and the specification of which parts of a molecule, if any, will be considered rigid in order to speed the calculation.
3. Specify conditions and computational details (14). For example, it may be necessary to specify parameters that define the solvent environment (e.g., water, chloroform, etc.) in which the molecules reside, or to determine whether the calculation will be precise and time-consuming versus crude and quick.
4. Start and monitor the calculation (16). This subtask may also include specifying which computer or computers will be used for the calculation, if more than one computer is available to the user.
5. View the results (18). This typically involves inspecting molecular conformations graphically in the context of numerical results and, potentially, creating a summary report of the results.

In another aspect of the present invention, a separate GUI is associated with each different subtask, as illustrated in FIG. 1 (20–28). In yet another aspect, the subtask GuIs are tailored for their specific subtasks in order to make them easier to use than the single all-purpose, conventional GUI of prior modeling methods. The subtask GUIs typically present the user with a combination of graphical representations of molecules, controls such as pull-down menus and tool icons, and numerical and graphical displays of quantitative data. The subtask GUIs may be tailored in various ways. In one aspect, each GUI is tailored by showing only controls required for the associated subtask. For example, the GUI for the first subtask listed above ("Load computer representation of molecules") does not need to show controls for running and monitoring the calculation or for viewing the results. Removing these unneeded controls makes it possible to present the user with a smaller number of controls and thus a simpler and less confusing interface, relative to conventional methods. It also makes it possible to display most or all of the controls relevant to the subtask simultaneously rather than placing many controls in pull-down menus where they are difficult for the user to find. In another aspect, different graphical representations of the molecules may be required in the different subtask GUIs. For example, the user could be shown a detailed representation of each molecule being loaded in Subtask 1 (10, 20), but only a simple molecular representations in a tabular format in Subtask 2 (12, 22). It should be noted that FIG. 1 shows only one possible division of a molecular modeling task. In general, the division should balance the advantages gained by simplification of the subtask GUIs against the complexity resulting from an excessively large number of subtasks.

Figure 2:
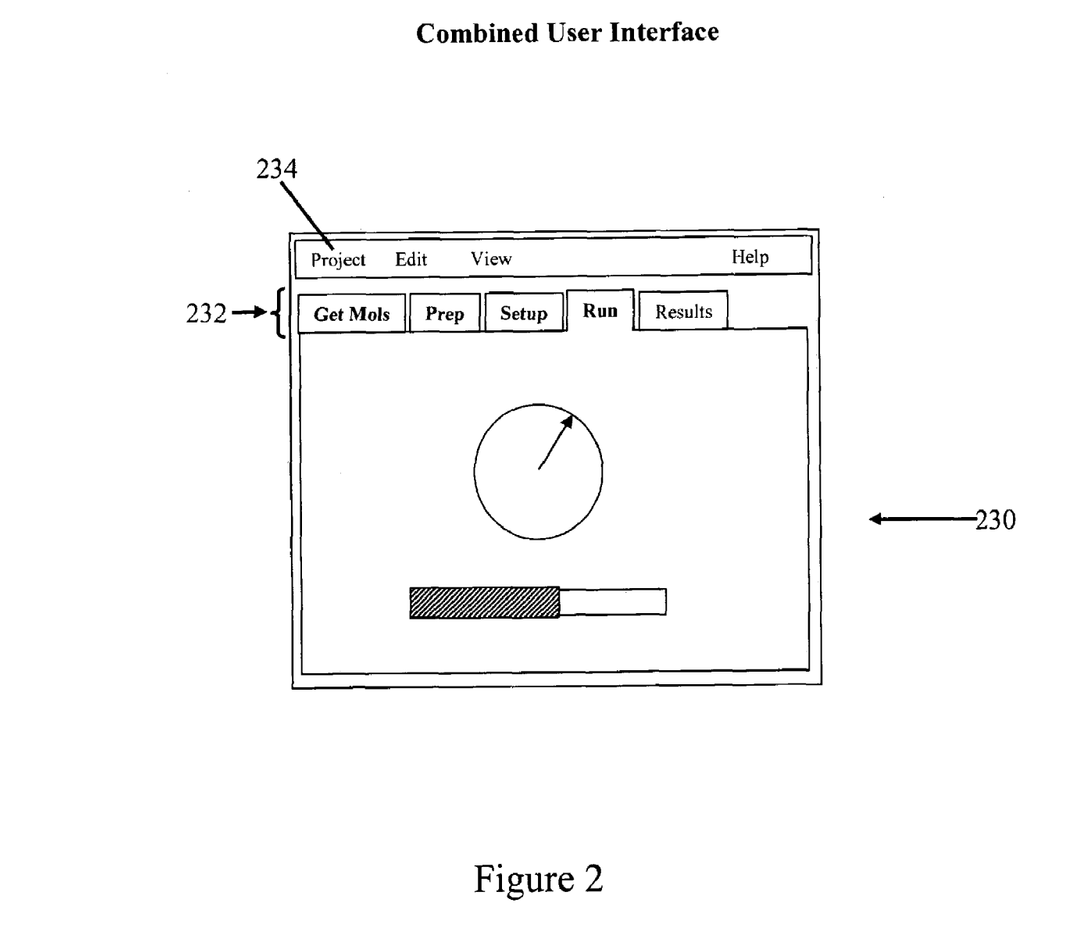
FIG. 2: Diagram of the assembly of the subtask GUIs into an overall GUI in which the individual subtask GUIs are accessed via tab icons. The subtask GUI for starting and monitoring the calculation is displayed.

In yet another aspect of the invention, the subtask GUIs are combined into a single overall GUI (230) which includes icons by which each subtask GUI can be selected for display and use, and in which these selection icons are arranged in the correct sequence for the overall task. FIG. 2 illustrates this aspect of the invention for the molecular modeling task introduced above, showing a preferred method in which the subtask GUIs are selected via tab icons (232). The tabs are arranged in the predetermined order of the subtasks, and clicking on a tab with a mouse or other computer pointing device causes the corresponding subtask GUI to be displayed. By this method, the user is provided with an overview of the sequence of steps required to carry out the calculation, and also with the freedom to deviate from the predetermined order when appropriate.

In yet another aspect of the invention, the information gathered or generated by each subtask is transferred automatically to the other subtasks that require the information, making it unnecessary for the user to perform the transfer manually. For example, in the calculation introduced in FIG. 1, the computer representations of molecules loaded in the first subtask (10) are transferred to all the other subtasks. As another example, the third subtask (14), which gathers the computational parameters selected by the user, transfers this information to the subtask for starting and monitoring the calculation. In another aspect of the invention, each subtask GUI is kept disabled until the information it requires has been transferred to it by the upstream subtasks, at which time it is enabled. When a subtask is disabled, clicking on its associated tab does not start the subtask application. In another aspect of the invention, whether a subtask GUI is enabled or disabled is conveyed graphically in the associated selection icon, for example by displaying the tab's text in black for an enabled GUI versus gray for a disabled GUI. In FIG. 2, the labels of enabled subtask GUIs are shown in bold face font and labels of disabled subtask GUIs are shown in normal font (32). Disabling subtask GUIs for which required information is not yet available prevents the user from attempting subtasks that are not yet feasible.

In another aspect of the invention, the method allows the user to return to the subtask GUIs associated with completed subtasks in order to review and revise what has already been done. For example, after the entire task has been completed, the user will typically view and analyze the results. In the example of FIG. 1, this is done via the Results GUI (28). However, the user may also need to review how the calculation was done in order to fully understand the results. In the tab icon example (232), the user can review the setup by clicking on the Setup tab and thereby displaying its associated GUI (24). This capability contrasts with conventional molecular modeling methods which provide no specific mechanism for reviewing the setup of a completed calculation. It should be noted that, if no safeguards were provided, this method would allow the user to complete a calculation and then go back and modify the calculation setup, thereby creating a situation in which the results displayed in the Results GUI (28) would not correspond to the setup displayed in the Setup GUI (24). In another aspect of the invention, this inconsistent and hence confusing status is prevented by allowing the user to view but not modify the setup once the calculation is complete. However, another aspect of the invention provides additional GUI elements in the overall interface, e.g. the Project menu (234), which allow the user to delete the calculation results and reenable the upstream subtask GUTs. In this way, the setup used for one calculation can easily be used as the starting point for another calculation. In another aspect, the invention also includes methods for saving a partial calculation setup, a complete calculation setup, or a complete calculation setup and the associated calculation results into a files on the hard drive so this information can be reexamined and reused.

The present invention also provides methods for reducing the expertise and work required to carry out a molecular modeling calculation by providing for partial automation of some of the subtasks. In one aspect, this is accomplished by providing the user with a control that causes the subtask to be executed automatically with standard methods and parameters. For example, in the second subtask (12) of the molecular modeling task diagrammed in FIG. 1, standard atomic parameters may be assigned automatically rather than requiring decisions from the user. The user is still free to modify the parameters assigned by the automated method, however. In another aspect of the invention, the results are made easier to use and share with others by generating a printable report of the results, rather than requiring the user to view and interpret the results only by viewing them through the graphical user interface. Optionally, the user is allowed to interactively select the information to be included in the report, and the format of the report. The present inventors believe that the subject invention represents the first molecular modeling method that allows generation of a printable report. This capability allows the results of the molecular modeling calculations to be shared more broadly. Also, in combination with the methods discussed above for enabling a novice to use the software, the report-generation capability makes it possible for a research supervisor to have a technician, rather than an expert computational chemist, run a calculation and bring back a useful report of the results.

Figure 3:
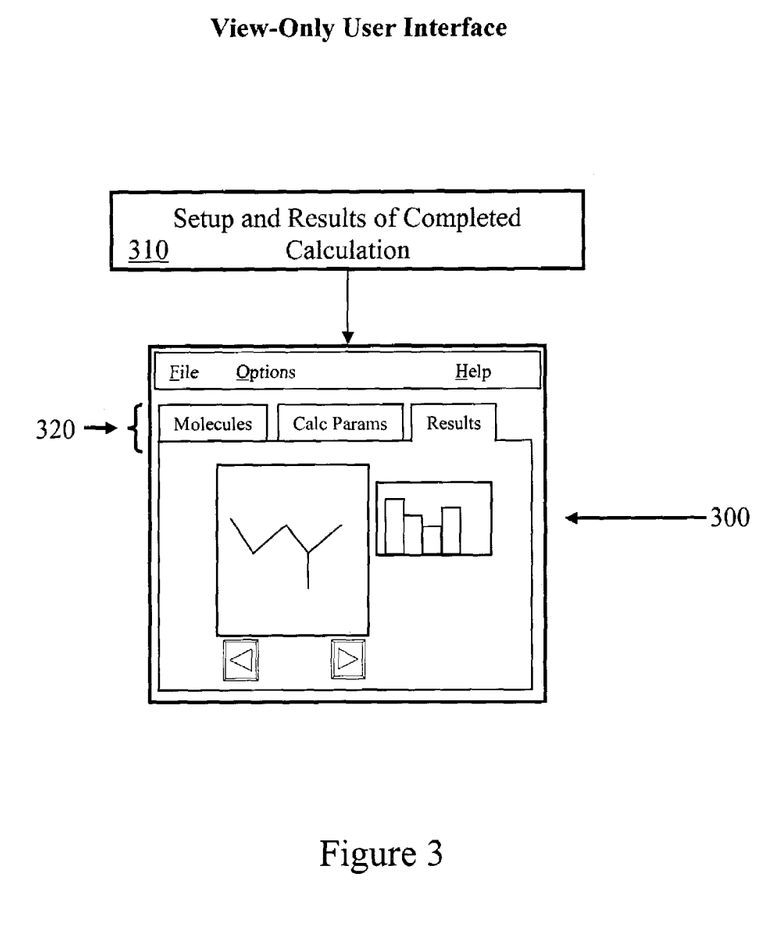
FIG. 3: Diagram of viewer GUI for viewing, but not modifying, the setup and results of a typical molecular modeling task according to the invention.

The present invention further provides a method for viewing the results of completed calculations with a software application that has a similar GUI but cannot carry out the actual calculations. FIG. 3 shows an example of such a viewer (300) for the molecular modeling calculation discussed above. This viewer loads (from the hard drive, for example) a file containing the information (310) from the full computational application (molecules, parameters, setup, and results) and allows the user to view the data via tab-linked GUIs (320). As shown in FIG. 3, fewer separate GUIs are typically needed in the viewer because it performs fewer functions than the full-fledged computational application. The advantage of such a viewer is that it enables a user who does not have the complete software application to study computational results in the context of the setup. Separating the viewing capability from the full computational capability enables a marketing strategy in which viewer software is distributed at low cost or for free, thus enabling customers who have purchased the full computational application to share their results widely. This strategy enhances the value of the fully functional software. The present inventors believe that the subject invention represents the first application of this strategy to molecular modeling software.

EXAMPLE

The present invention was used in a software application for calculating the stable 3D conformations of a drug-like ligand in a macromolecular (e.g., protein) binding site. This type of calculation is of substantial interest in the pharmaceutical industry because of its relevance to computational drug design. The algorithm (J. Comput. Chem. 23:1656–1670, 2002) is based upon statistical thermodynamics, which states that the most probable conformations of a molecule or molecules are those of lowest energy. If the conformation of a receptor-ligand complex is specified by a set of 3D atomic coordinates r and is of energy E(r) then the probability density associated with a conformation is given by the Boltzmann distribution: $p(r)=\exp[-E(r)/kT]/(\int \exp[-E(r)/kT] dr)$. In the present application, the energy is computed via an empirical energy model such as CHARMM (e.g., J. Phys. Chem. B. 102:3586–3616, 1998), AMBER (J. Am. Chem. Soc. 106:765–784, 1984; J. Am. Chem. Soc. 117:5179–5197, 1995) or Dreiding (J. Phys. Chem. 94:8897–8909, 1990), enabling the energy of a given conformation to be evaluated in a small fraction of a second on a computer. Such models compute the energy as $E(r)=E_{dihed}(r)+E_{electrostatic}(r)+E_{vanderWaals}(r)$; where $E_{dihed}(r)$ accounts for the variation of the energy intrinsic to dihedral bond rotations, $E_{electrostatic}(r)$ accounts for the electrostatic interactions among atoms, and $E_{vanderWaals}(r)$ accounts for the van der Waals interactions among all atoms. (Bond lengths and angles, which also influence the energy, are held fixed in the present algorithm; this simplification is justified by the rigidity, or near invariance, of these geometric parameters.) Our current implementation of this algorithm uses AMBER, CHARMM and/or Dreiding, but other empirical energy models should also be effective. Applying any of these energy models to a molecular system requires assigning the correct atomic parameters to each atom; for example, each atom is typically assigned a small electrical charge to account for its polarity.

The algorithm employed in conjunction with the present example seeks the most probable conformations by an automated search for conformations whose energy is especially low. A conformation is defined by a set of dihedral angles associated with rotatable chemical bonds, along with 6 additional variables that specify the position and orientation of the ligand within the receptor binding site. In order to speed the optimization, the receptor is approximated as rigid. (We have implemented a version that allows selected chemical groups of the receptor to be mobile, but the simpler version described here suffices to exemplify the present invention.) This simplification reduces the complexity of the search for low-energy conformations. It also makes it possible to speed the evaluation of the energy of each conformation by reducing the number of pairwise interatomic distances that must be computed when evaluating the electrostatic and van der Waals interaction energies, as described above. The reduction is accomplished by precomputing an electrostatic and a van der Waals field of potentials generated by the receptor (J. Comput. Chem. 6:432–436, 1985). This potential field is computed only once because it does not change during the search for low-energy structures. It is stored via a cubic lattice of grid points, each of which is associated with the field generated at that point by the receptor. The field felt by each atom of the ligand in a given conformation is computed by interpolation from the values at the closest grid points.

Figure 4:
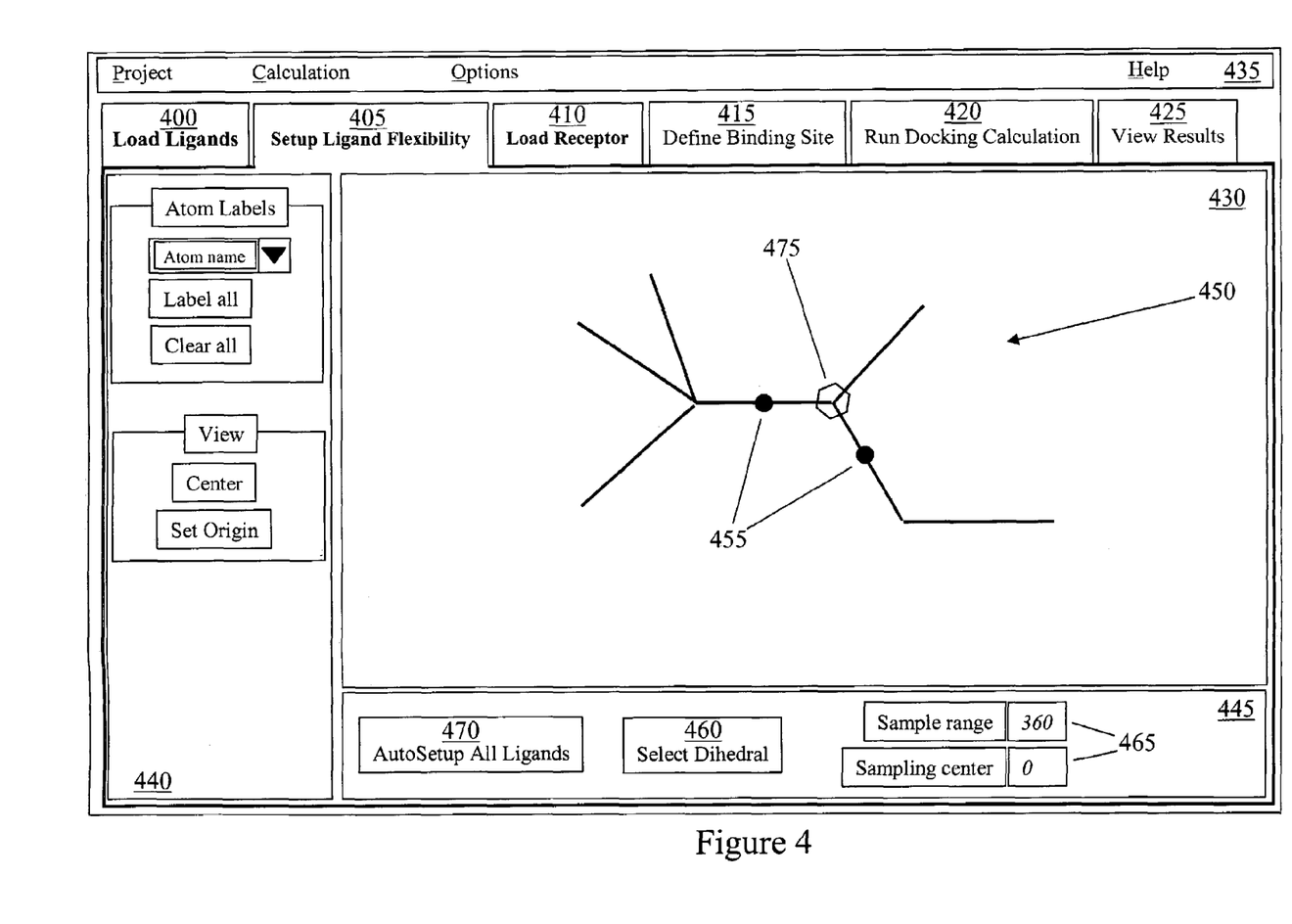
FIG. 4: Diagram of GUI according to the invention for the example task of computing the stable 3D conformations of a set of small compounds in the binding site of a receptor of known 3D structure.
Figure 5:
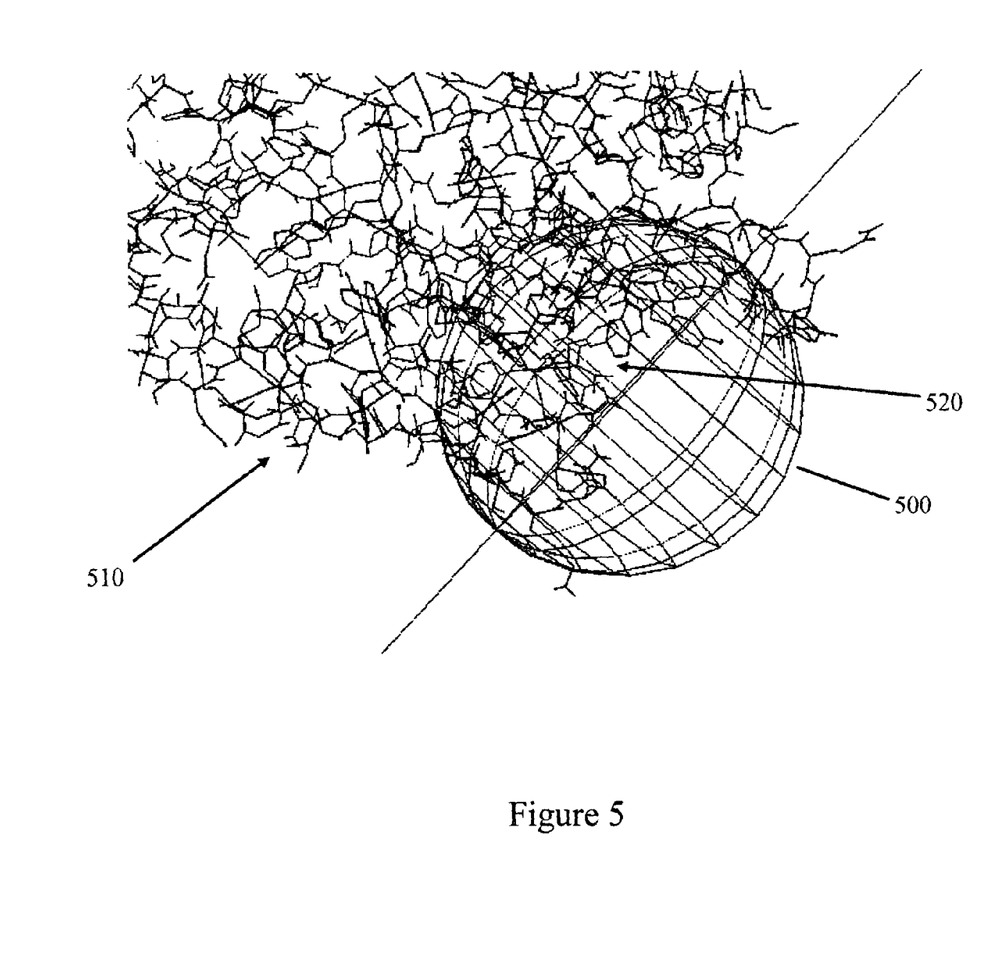
FIG. 5: Illustration of method for selecting atoms or other molecular components by interactively positioning and sizing a 3D shape.

FIG. 4 diagrams a GUI for this algorithm that uses the present invention. For illustration, the diagram has been simplified somewhat relative to the actual GUI. The overall task is subdivided into 6 subtasks, each of which is associated with a tab icon in the overall GUI. In FIG. 4, the Setup Ligand Flexibility subtask GUI is displayed, as further discussed below. The tabs associated with subtasks that are enabled are labeled in bold face font (400, 405, 410) and the tabs associated with subtasks that are not yet enabled because information from previous subtasks is not yet available are labelled in normal font (415, 420, 425). In each subtask GUI, molecules are displayed in a central pane (430), controls that are common to multiple subtask GUIs are collected in the menu bar above the tabs (435) and in the left-hand pane (440), and controls that are specific to each subtask GUI are collected in the bottom pane (445) and an optional right-hand pane (not shown in Figure). The subtasks are as follows:

1. Load Ligands (tab 400). Computer representations of the ligands to be studied are loaded into the application. This subtask GUI provides a standard file browser and a 3D molecule viewer.
2. Setup Ligand Flexibility (tab 405). This subtask is used to establish which parts of the ligands will be treated as flexible for the purposes of the calculation, where flexibility is determined by which bond dihedrals (i.e., torsion angles) are considered to be rotatable. FIG. 4 shows a ligand (450) in the center pane (430). The two bonds with filled circles at their midpoints (455) will be considered rotatable during the calculation. Tools along the bottom panel (445) allow the user to choose which bonds will be considered rotatable (460) and to specify the centers and ranges of the dihedral rotations in degrees (465). In most applications, however, users will simply use the Auto Setup All Ligands button (470) to run an automated procedure for selecting which bonds will be treated as rotatable. The hexagon (475) centered on one of the atoms defines the translational center or "handle" of the ligand; this becomes important in the Define Binding Site subtask (tab 415). Note that the controls unique to the Setup Ligand Flexibility subtask are all visible to the user in the lower pane (445), rather than being hidden under multifunctional pull-down menus, as is customary in conventional molecular modeling GUIs.
3. Load Receptor (tab 410). The next subtask is to load a computer representation of the receptor—usually a protein—to which the ligands will be fitted computationally. This GUI provides a file browser and a 3D molecule viewer, and, optionally, tools for assigning parameters and computing the 3D structures of parts of the receptor for which inadequate 3D structural information is available.
4. Define Binding Site (tab 415). The next subtask is to define the spatial region of the receptor to which the ligands will be fitted computationally. This is accomplished via the Define Binding Site GUI which provides controls enabling the user to designate a search region as a rectangular parallelopiped (a box) that encompasses the region of the receptor expected to bind the ligands. During the subsequent calculation, the center of translation or "handle" of each ligand (475) is constrained to remain within the box. Specialized controls at the bottom of the window enable the user to adjust the position, orientation and dimensions of the box, and to view the box in the context of the ligands.
5. Run Docking Calculation (tab 420). The next subtask is to set additional parameters for the calculation and to start, monitor and, optionally, terminate the calculation. The GUI displays a default set of computational parameters that the user can adjust, along with controls to start and terminate the calculation and a progress bar that shows how much of the calculation is complete. The ligand-receptor conformations that have been generated to date are displayed in a 3D graphical pane.
6. View Results (tab 425). After at least one conformation has been computed, the final subtask GUI, View Results, is enabled so that the results to date can be viewed and analyzed. Controls at the bottom of the GUI window allow the user to select which ligand to study and which conformation(s) of the ligand are displayed in the central graphical pane. Numerical and graphing displays in the right pane permit the user to interpret the graphically displayed conformations in the context of numerical energies and energy components. For example, it may be of interest to know that a given conformation is stable—i.e., low in energy—because of especially favorable electrostatic interaction energies with the receptor. Tools for selecting what part(s) of the macromolecule and the ligands will be displayed, and in what format they will be displayed, are available on the left pane. The selection tools include a 3D atom-selector tool, illustrated in FIG. 5, that allows the user to interactively position and resize a closed 3D form, such as the sphere (500) shown in the illustration, while viewing the form and the molecule(s) (510) in real time; atoms enclosed in the shape (520) are considered "selected. The present inventors believe that this selection tool is novel and particularly advantageous as a means of selecting specific atoms in a complex 3D system. Tools for generating a summary report are also provided.

Further Illustrative Applications of the Invention

It is expected that, based on the description provided herein, those of skill in the art would have no difficulty applying the tools and methods of the subject invention to most if not all tasks employed in computational chemistry and molecular modeling. Without narrowing the scope of the subject invention, which is solely defined by the appended claims, the example above and discussion below illustrate selected embodiments of the invention.

One application of the subject invention relates to the computational selection of compounds likely to bind a macromolecular receptor with high affinity. Such calculations are of especial interest in structure-based drug-discovery, where the goal is to identify a compound that can tightly bind and inactivate a macromolecule involved in a disease process; e.g., HIV protease. Here, as in the example above, the user supplies a list of drug-like compounds and the 3D structure of a macromolecular receptor and computes the low-energy 3D conformations of the ligand-receptor complexes. These 3D conformations are then used as a basis for calculating affinities via one or more scoring functions, such as that in J. Med. Chem. 42:791–804, 1999. It is envisioned that the GUI will enable the user to use multiple scoring functions simultaneously because it has been shown that this so-called consensus scoring approach can improve accuracy (J. Med. Chem. 42:5100–5109, 1999). The subtasks and their associated GUIs are similar to those in FIG. 4, except that the Results subtask GUI provides controls for computing affinities and viewing these additional results. In particular, the View Results GUI shows the user a list of the top-scoring ligands. The present software application may, also or alternatively, be outfitted with relatively sophisticated energy models that calculate binding free energies via, for example, continuum models of the solvent (e.g., J. Phys. Chem. 97:1101–1109, 1993) and free energy integration methods (e.g., J. Phys. Chem. 101: 1609–1618, 1997). Using these methods will require additional GUI elements and analysis tools.

The present invention can also be used in the automated design of new compounds that bind a selected receptor of known 3D structure. Such calculations are useful in drug-discovery for at least the reasons noted above. Algorithms for automated ligand design have been described in the literature, as in J. Chem. Inf. Comput. Sci. 34:207–217, 1994. These algorithms typically involve specifying a collection of chemical fragments along with rules for linking them to form stable compounds. Fragments are computationally fitted into the receptor binding site and linked to form compounds that are expected to bind the receptor with high affinity, based upon scoring functions and/or energy models. A natural division into subtasks would be as follows:

1. Load receptor. This GUI provides a file browser and a 3D molecule viewer, as well as tools for assigning parameters and computing the 3D structures of parts of the receptor for which adequate 3D structural information may not be available.
2. Load fragment library. Tools are provided for loading the library of chemical fragments and the linking rules from a file on the hard drive or elsewhere. Optionally, tools are provided for defining a new fragment library and its associated rules.
3. Define binding site. The spatial region of the receptor to which the designed ligands are to bind is defined by the user, as discussed in the Example above.
4. Design ligands. Parameters controlling, for example, the allowed size and other characteristics of the designed compounds, the thoroughness of the ligand optimization, etc., are established by the user. Tools are provided to start, monitor and optionally terminate the calculation.
5. View results. 3D graphical representations of the designed ligands are shown in the context of the receptor binding site, computed measures of their affinity, etc.

The present invention also provides a method that can be used in calculating the thermodynamically stable conformations of one or more user-supplied molecules; e.g., drug-like compounds, macrocycles such as cyclophanes and crown ethers; oligomers of various types; etc. Such conformational analysis calculations are useful in predicting molecular properties and hence in the design of compounds for various purposes, such as drugs; small synthetic receptors ("hosts") for binding, stabilizing or solubilizing other small molecules ("guests"); catalysts; and polymers. As in the example above, each molecule is assigned energy parameters, and an optimization algorithm is used to search for the lowest-energy conformations. Examples of such algorithms have been described in the scientific literature, such as J. Chem. Phys. 105:7868–7871, 1996. A natural division into subtasks according to the present invention would be:

1. Load compounds. Computer representations of the compound(s) to be studied are loaded into the application.
2. Prepare compounds. Assign parameters and allow user to establish which part(s) of the molecule(s) are considered flexible.
3. Run conformational search. Set search parameters, initiate, monitor, and optionally terminate calculation.
4. View results. View the computed conformations along with their energies and energy components (e.g., electrostatic, van der Waals.)

The present invention also provides a method that can be used in determining the 3D structure of a protein (the target) whose amino acid sequence is known from experiment but whose 3D structure has not been determined experimentally. In the most accurate approaches, known as homology modeling or comparative modeling (see, e.g., Prot. Struct. Func. Gen. Suppl 1:14–28, 1997), the unknown structure is determined by comparison with one or more other proteins (the templates) whose amino acid sequences are similar to that of the target and whose 3D structure is known from experiment. The following subtasks are envisioned.

1. Load target sequence. The amino acid sequence of the protein whose structure is to be determined is obtained from the hard drive, the WWW, or another data resource.
2. Find templates. The Protein Data Bank (PDB: www.pdb.org) and/or other sources of protein 3D structures are searched for proteins whose amino acid sequences are similar to that of the target. Greater than 60% identity is preferred for the sake of accuracy, but lower identities can still yield useful structures.
3. Align sequences. Stretches of identical or similar amino acid sequence in the templates and target proteins are matched with each other by existing algorithms, such as Nucl. Acids Res. 22:4673–4680, 1994.
4. Compute structure. The main-chain and side-chain conformations of the most similar template(s) are assigned to the target in regions where the target sequence is well aligned with the template(s). Parts of the target sequence for which there is no matching template sequence are assigned arbitrary conformations, or have their conformations computed by other means, such as a search for low-energy conformations (see above). If the calculation is lengthy, the subtask GUI will provide controls for monitoring and terminating it.
5. View structure. A 3D graphical representation of the target structure and its sequence is displayed and tools are provided for comparing the target with the template(s) used to compute its structure.

We claim:

1. A method of carrying out a molecular modeling calculation and displaying the results thereof through a task-oriented user interface, which allows for the individual user to calculate the properties of at least one selected molecule in a series of steps the results of which individual steps are visualizable by the individual user, wherein the method comprises the following steps a. an individual user accesses a molecular modeling interface that subdivides the calculation of molecular properties for a selected molecule into subtask steps which are conducted through controls and graphics that provide for conducting a specific selected subtask according to a predetermined sequence;
b. the individual user selects the controls and/or graphics and carries out the subtask using said individualized subtask user interface for a selected molecule; and
c. the information generated from the selected subtask for the selected molecule is thereafter transferred to a subtask positioned downstream in the sequence from the selected subtask;

whereby the foregoing steps allow for an individual user to conduct a molecular modeling calculation for a selected molecule such that the calculation of molecular properties for a selected molecule is subdivided into a predetermined sequence of subtasks using graphics and controls which allow the individual user to carry out a selected subtask while allowing the controls and/or graphics associated with non-selected subtasks to remain accessible but not displayed.

2. The method of claim 1 further comprising showing only preselected controls for a selected subtask.

3. The method of claim 1 further comprising showing only preselected graphics for a selected subtask.

4. The method of claim 1 further comprising combining two or more subtask user interfaces in a multiple-subtask user interface.

5. The method of claim 4 further comprising providing subtask selection controls that are always visible in the multiple-subtask user interface.

6. The method of claim 5 wherein the subtask selection controls in the multiple-subtask user interface are arranged according to the predetermined sequence of subtasks.

7. The method of claim 1 further comprising enabling the controls and graphics associated with a subtask only after the calculation steps associated with an upstream subtask are completed.

8. The method of claim 7 further comprising combining two or more subtask user interfaces in a multiple-subtask interface.

9. The method of claim 8 further comprising providing subtask selection controls that are always visible in the mutiple-subtask user interface.

10. The method of claim 9 further comprising displaying the subtask selection controls differently when the associated subtask is enabled versus when it is disabled.

11. The method of claim 1 wherein the selections and/or intermediate results from the subtasks are viewable.

12. The method of claim 1 further comprising disabling a subtask user interface, whereby correct correspondence between the calculation setup and the results is maintained.

13. The method of claim 1 further comprising clearing the settings and results downstream from a selected subtask and resuming setup and calculations from the selected subtask.

14. The method of claim 1 further comprising storing settings and results to a storage medium.

15. The method of claim 1 wherein a subtask user interface or a control in a subtask user interface is hidden and the associated subtask is executed automatically.

16. The method of claim 1 ftuther comprising generating a printable report of the results.

17. A method of viewing results of calculations carried out according to claim 1 comprising providing a user interface that enables the calculation setup to be viewed along with the final results, but does not enable changes to the calculation setup or execution of the calculation.

18. The method of claim 1 wherein the molecular modeling calculation comprises predicting the three-dimensional conformation of a user-selected compound bound to a user-selected macromolecule of known three dimensional structure.

19. The method of claim 18 further comprising allowing the user to define the three dimensional part of the macromolecule to which a compound may bind by interactively positioning, resizing and/or reshaping a three dimensional object that delimits the part of the macromolecule to be studied, while viewing both the macromolecule and the three dimensional object in real time.

20. A method of selecting molecular parts in calculations carried out according to claim 1 comprising allowing the user to interactively position a three dimensional closed object while viewing both the object and the molecular system and wherein atoms enclosed by the form, or molecular components partly enclosed by the form, are considered to be selected.

21. The method of claim 1 wherein the molecular modeling calculation comprises determining from a user-supplied list those compounds with higher binding affinity for a user-selected macromolecule of known three-dimensional structure.

22. The method of claim 1 wherein the molecular modeling calculation comprises generating the chemical composition and structure of a compound likely to bind to a user-selected macromolecule of known three-dimensional structure.

23. The method of claim 1 wherein the molecular modeling calculation comprises determining the thermodynamically stable conformations of one or more user-supplied set of molecules.

24. The method of claim 1 wherein the molecular modeling composition comprising determining a three-dimensional structure of a user-defined protein based upon a known three-dimensional structure of a chemically similar protein.

* * * * *